US00PP19224P3

(12) United States Plant Patent
Duncan

(10) Patent No.: US PP19,224 P3
(45) Date of Patent: Sep. 16, 2008

(54) **SEASHORE *PASPALUM* PLANT NAMED 'TE-13'**

(50) Latin Name: *Paspalum vaginatum*
Varietal Denomination: TE-13

(75) Inventor: Ronny R. Duncan, Boerne, TX (US)

(73) Assignee: Turf Ecosystems, LLC, Naples, FL (US)

( * ) Notice: Subject to any disclaimer, the term of this patent is extended or adjusted under 35 U.S.C. 154(b) by 1 day.

(21) Appl. No.: 11/582,541

(22) Filed: Oct. 18, 2006

(65) Prior Publication Data

US 2008/0134400 P1 Jun. 5, 2008

(51) Int. Cl.
*A01H 5/00* (2006.01)

(52) U.S. Cl. ..... Plt./387

(58) Field of Classification Search ..... Plt./387, Plt./388
See application file for complete search history.

(56) References Cited

U.S. PATENT DOCUMENTS

| | | | |
|---|---|---|---|
| PP3,939 | P | 8/1976 | Whiting |
| PP12,625 | P2 | 5/2002 | Duncan |
| PP12,665 | P2 | 5/2002 | Duncan |
| PP13,100 | P2 | 10/2002 | Bennett et al. |
| PP13,105 | P2 | 10/2002 | Bennett et al. |
| PP13,294 | P3 | 12/2002 | DePew et al. |
| 7,262,341 | B1 | 8/2007 | Fricker et al. |
| 2007/0089214 | P1 | 4/2007 | Duncan |

*Primary Examiner*—Annette H Para
*Assistant Examiner*—S. B. McCormick-Ewoldt
(74) *Attorney, Agent, or Firm*—Hunton & Williams LLP

(57) ABSTRACT

A new and distinct cultivar of *Paspalum vaginatum* Swartz (Seashore *paspalum*) named 'TE-13' is disclosed. 'TE-13' is characterized as having exceptional turf density and foliarly disease resistance under closely mowed micro-environmental stress conditions.

2 Drawing Sheets

Botanical classification: *Paspalum vaginatum* Swartz.
Variety/cultivar denomination: 'TE-13'.

BACKGROUND OF THE INVENTION

The invention relates to a new, distinct and stable cultivar of *Paspalum vaginatum* Swartz and hereafter referred to by the cultivar denomination 'TE-13'.

*Paspalum vaginatum* Swartz (commonly referred to as "Seashore *paspalum*") is a grass in the Panicoideae subfamily that inherently colonizes moist euryhaline to stenohaline ecosystems, e.g., along coastal venues and brackish sands or silty areas. This warm-season perennial grass species is ecologically aggressive and varies in leaf texture from very coarse wild indigenous native ecotypes to intermediate to finer-leaved turf ecotypes for uses ranging from land reclamation, dune stabilization, bioremediation (phytoaccumulation) to forages and recreational turf. The diploid, 20-chromosome turfgrass produces both rhizomes (primarily) and stolons (secondarily) for asexual reproduction and dispersion; it is self-incompatible and rarely produces viable seed in monostands, and only when very strict genetic and environmental conditions are satisfied. The grass can tolerate periodic meso-haline flooding encompassing waterlogged, low oxygen conditions.

*Paspalum vaginatum* has been found in more than 35 countries in Europe, Africa, temperate and tropical Asia, Australia, Pacific Rim, South America, Central America, Caribbean region, North America and in countries located near the Mediterranean Sea. The primary center of origin for the turfgrass types is South Africa and a secondary center of origin is Brazilian and Argentinean coastal areas. Wild, native coarse-textured types can be found along Atlantic, Gulf of Mexico, and Pacific coastal USA saline venues, while the naturalized turfgrass types are predominately localized along the eastern Atlantic coastline. With increasing demands on human use of potable water and the mandated use of alternative non-potable water resources (effluent or recycled water, saline ground and surface water) on recreational turf, turfgrasses that can tolerate a variable range of irrigation water salinities from mildly saline to brackish, that require and efficiently utilize judicious fertilizer applications, and that are pest resistant with multiple inherent genetic stress tolerances are needed for environmental stewardship and ecosystem sustainability.

BRIEF SUMMARY OF THE INVENTION

The present invention relates to a new and distinct cultivar of *Paspalum vaginatum* Swartz and hereafter referred to by the cultivar denomination 'TE-13'. The 'TE-13' cultivar is particularly suited as a semi-dwarf warm season turfgrass for recreational fields, golf courses, parks, landscapes, and as one potential parent for hybrid seed production.

The following traits have been consistently observed and are determined to be the combination of unique characteristics that distinguish 'TE-13' as a new and distinct cultivar:

1. A semi-dwarf growth habit that tolerates a wide range (0.070 to 1.500 inches or 1.75 to 37.5 mm) of mowing heights with excellent turfgrass canopy density and quality traits for use on all areas of golf courses or sports fields.
2. Establishes rapidly and finalizes grow-in from surface stolons aggressively. The horizontally creeping stolons are shorter and more uniformly bunched during grow-in compared with other *paspalum* cultivars.

3. Consistently tolerates irrigation water levels with total dissolved salts (TDS) ranging from about 4000 to about 6000 ppm under mowing heights on golf course greens about <3 mm. The cultivar can tolerate higher salinity levels with proper salt management and the installation of appropriate infrastructure improvements in the ecosystem for long term sustainability.
4. Produces very few seed heads (inflorescence) in response to day length/photoperiod changes or environmental (drought, cold, traffic) stress exposure compared to other *paspalum* cultivars currently on the market.
5. DNA profile analysis demonstrating distinct genetic separation from *paspalum* cultivars currently on the market. The analysis indicated that 'TE-13' was not closely related to 'SeaIsle 2000' or 'Salam'™ and is a genetically distinct and unique cultivar.
6. Dark green genetic color identical to 'SeaIsle 2000' and much darker green than 'SeaIsle Supreme', 'SeaIsle 1', 'Seadwarf' or 'Salam'™.
7. Finalizes grow-in from surface stolons more aggressively than 'SeaIsle 1' and 'SeaIsle 2000' and similar to 'SeaIsle Supreme'.
8. Shows exceptional turf density similar to 'SeaIsle 2000' and better than 'SeaIsle 1'.
9. Good resistance with proper management to foliar diseases such as dollar spot, fusarium blight and brown patch.

DETAILED BOTANICAL DESCRIPTION

Figure 1:
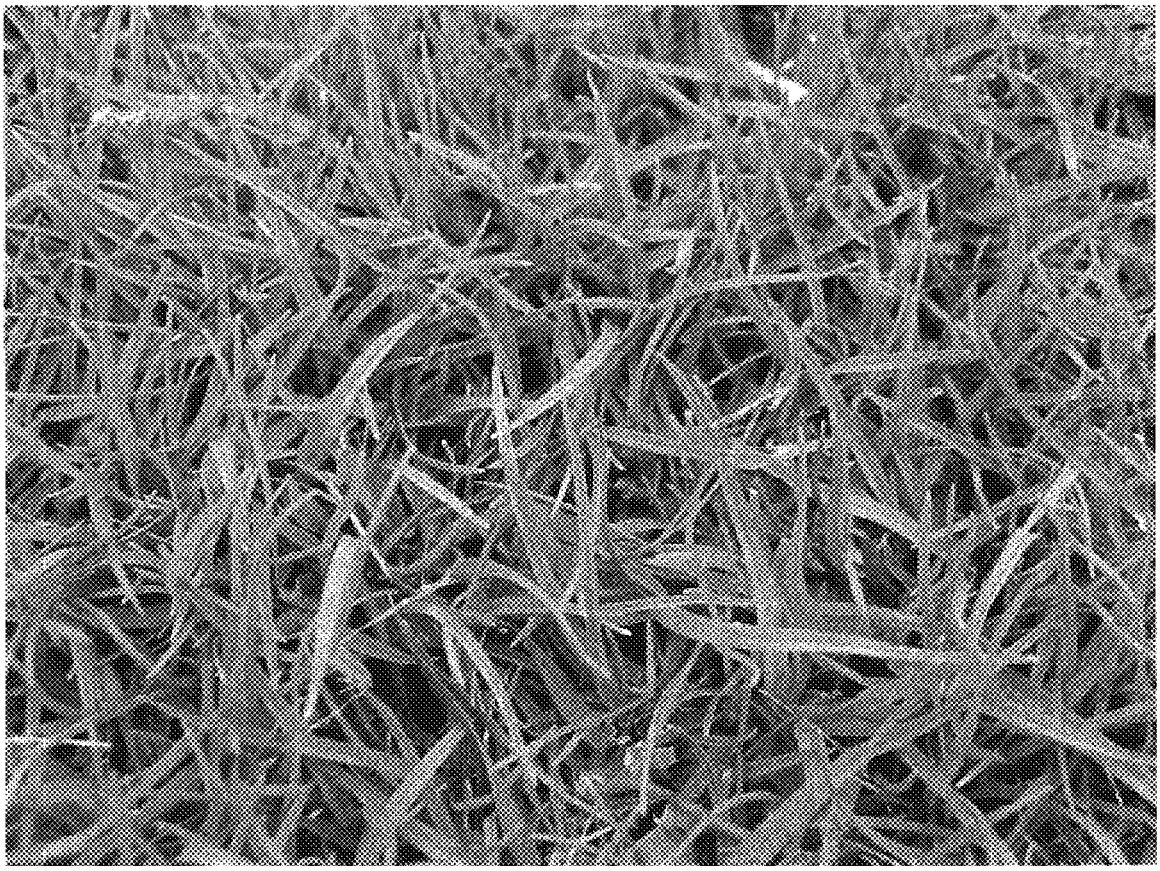
FIG. 1 is a photograph of the typical cosmetic appearance of 'TE-13'.
Figure 2:
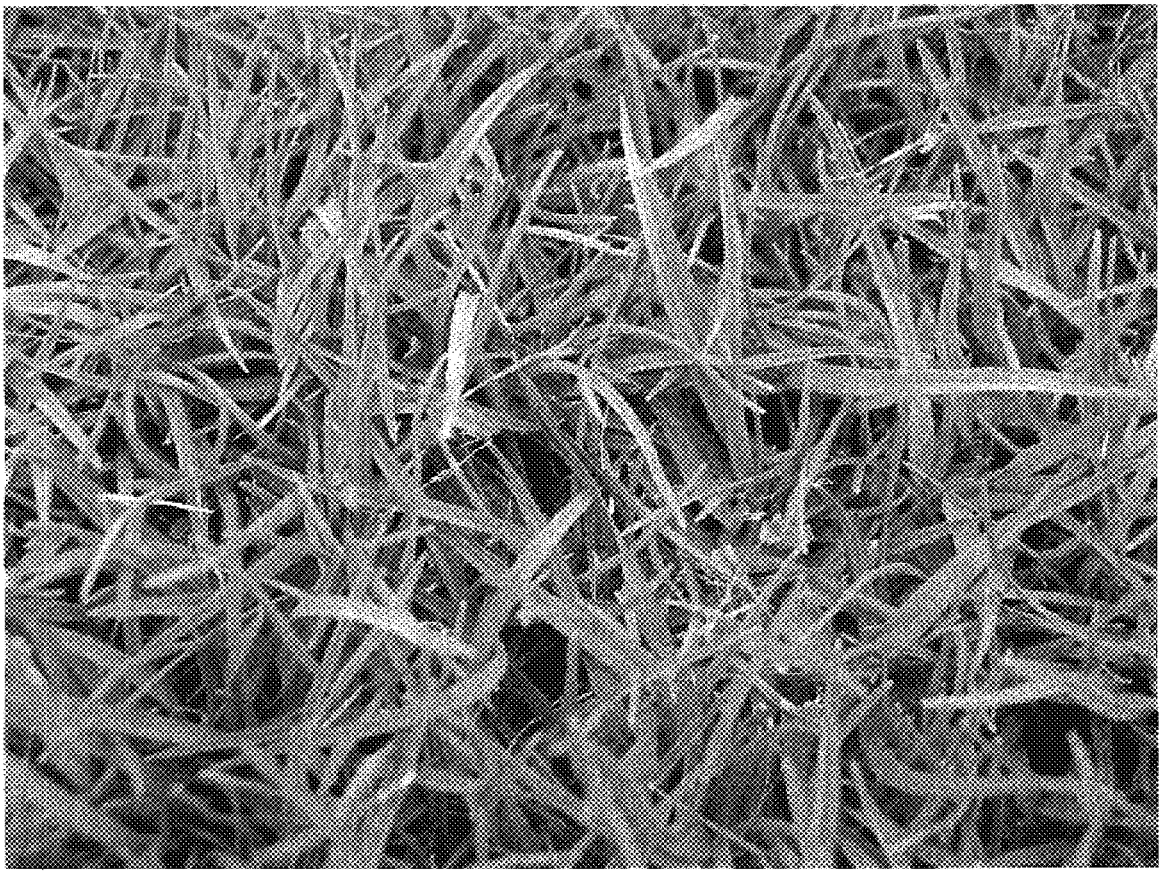
FIG. 2 is another photograph of the typical cosmetic appearance of 'TE-13'.

'TE-13' was selected from a U.S. Golf Association-specified golf course green in Naples, Fla. that had been continuously mowed at less than 3 mm height under constantly about >90% relative humidity conditions and temperatures about >30° C. (about >90° F.). The selection visually exhibited exceptional turf density and fungal disease resistance when the grass around it was being attacked by pathogens causing brown patch and fusarium blight; the green was managed under close mowed (about 0.070 or about 1.75 mm) micro-environmental stress conditions. 'TE-13' is suspected to be a natural mutation of an unknown parent.

Asexual reproduction was carried out using stolons or rhizomes and nodal segments, which inherently exist in the plant. Plants of the claimed cultivar were extracted from a mature planting, the soil was removed and the plant segments were separated into a plantlet with some root system attached or actual unrooted nodal segments from stolons or rhizomes (collectively referred to as "sprigs"). The sprigs were planted in soil. New plants grew from the stolons or rhizomes and nodal segments of the sprigs and were observed for uniformity in plant characteristics.

'TE-13' was asexually reproduced after initial selection with no off-types or further suspected mutations occurring. The subsequent multiple increased from the initial selected propagule in both the breeding block (100 feet×30 feet) and all subsequent plantings for evaluations over locations revealed only a true-to-genotype cultivar. No off types were observed at any time. Therefore, the plants asexually reproduced remained true to type. The initial plantings in either pots in the greenhouse or swards in the field involved only monostands and no subsequent pollination or seed set was observed at any time during the generation increases of this cultivar.

The initially selected asexual propagule was planted in a greenhouse in mid-Florida (latitude 27° 12' and longitude 81° 51'); then it was transplanted to 3 m×3 m replicated plots in mid-Florida and eventually in a 4 m×4 m plot on a golf course in Naples, Fla. for side by side comparisons with 'SeaIsle 2000' (described in U.S. Plant Pat. No. 12,625) and 'SeaIsle Supreme' (described in U.S. Pub. No. 2007/0089214), and in a 1.5 m×1.5 m plot north of San Antonio, Tex. on calcareous native clay soils. The selection was evaluated for turf quality and related traits using rotary mulching mowers at 0.75-1.0 inch (18.75-25.00 mm mowing height) at the San Antonio, Tex. location. A genetic 'breeder block' was established in mid-Florida on sandy soil and plugs were sent to New Mexico State University for initial field turfgrass plot testing with other grasses in Las Cruces, N. Mex. The age of the sward (10×10 feet) in the field plots and greenhouse pots that were measured for detailed botanical descriptions below were 2 and 1 year(s) old, respectively.

BOTANICAL DESCRIPTION $4^{th}$ Leaf blade length and width; length of sheath: Greenhouse measurements=about 0.86 cm $4^{th}$ leaf length; about 0.23 cm $4^{th}$ leaf blade width; sheath length=about 0.56 cm.

*Field plot measurements.*—About 0.60 cm $4^{th}$ leaf blade length; about 0.35 cm $4^{th}$ leaf blade width; sheath length=about 0.53 cm.

*Comparative data for 'SeaIsle 2000' on field plot measurements.*—About 0.60 cm, about 0.245 cm, about 0.575 cm.

$4^{th}$ Internode stolon (stolon nodes are distinctly pubescent and the pubescence is whitish in colour) length and diameter; leaf blade length and width; sheath length: Greenhouse measurements=about 1.21 cm $4^{th}$ internode stolon length; about 0.155 cm $4^{th}$ internode stolon diameter; about 1.01 cm leaf blade length; about 0.195 cm leaf blade width; about 0.84 cm leaf sheath length.

*Field measurements.*—About 0.595 cm $4^{th}$ internode stolon length; about 0.225 cm $4^{th}$ internode stolon diameter.

*Comparative data with 'SeaIsle 2000' on field plot measurements.*—About 0.62 cm $4^{th}$ internode stolon length; about 0.290 cm $4^{th}$ internode stolon diameter.

Leaf veins: obscure; leaf margins; smooth. Leaves are narrower and smaller than 'SeaIsle Supreme', 'SeaIsle 2000', and 'SeaIsle 1'.

Auricles were absent. Mid-culm leaves do not have sheath or blade auricles, are distinctly distichous, are linear and glaborous, and gradually taper to a narrow apex.

Ligule: <1 mm, membranous, and truncate (pubescent from behind). Collar is normal and smooth.

Inflorescence: Twin spikes (dual conjugate racemes on the primary branch) on mainly basally decumbent, erect and branched culms with glaborous nodes. Peduncle is shorter and smaller than 'SeaIsle Supreme'. Glumes are glaborous, nerved, and awnless. Each spikelet is solitary, plano-convex, subsessile, and elliptic. No actual seed development was observed during evaluation trials of this cultivar.

Salt tolerance and growth rates: Observable salt tolerance response on greens irrigated continuously with >5000 ppm water was equal to 'SeaIsle 2000', better than 'SeaIsle 1', and less than 'SeaIsle Supreme' (See Table 1). Aggressive growth rate is slightly less than 'SeaIsle Supreme', but greater than 'SeaIsle 2000' and slightly greater than 'SeaIsle 1' (See Table 2).

TABLE 1

| Relative Salt Tolerance Rankings | |
|---|---|
| 'SeaIsle Supreme' | 9.0 (highest) |
| 'SeaIsle 2000' | 7.5 |
| 'TE-13' | 7.5 |
| 'SeaIsle 1' | 7.0 |
| 'Salam' ™ | 5.0 (medium) |

TABLE 2

| Relative Aggressiveness (Growth Rate) | |
|---|---|
| 'SeaIsle Supreme' | 9.0 (highest) |
| 'TE-13' | 8.0 |
| 'SeaIsle 1' | 7.0 |
| 'SeaIsle 2000' | 5.0 |
| 'Salam' ™ | 4.0 |

Turf colour: Colour was determined by comparison of at least 5 randomly selected leaf blades for grass that was maintained under USGA specification greens management conditions mowed at 0.110 inch height of cut. The same protocol was used for 'SeaIsle 1' and 'SeaIsle 2000'.

TABLE 3

| Royal Horticultural Society Colour Chart: | |
|---|---|
| 'TE-13' | 137A (Dark Green) |
| 'SeaIsle 2000' | 137A |
| 'SeaIsle 1' | 137B |
| 'Adalayd' | 138A |
| 'SeaIsle Supreme' | 137C (Green) |
| 'Salam' ™ | 137C |

'SeaIsle 2000', 'SeaIsle 1' and 'Adalayd' are described in U.S. Plant Pat. Nos. 12,625, 12,665 and 3,939, respectively. 'SeaIsle Supreme' is described in U.S. Pub. No. 2007/0089214.

Turf quality:

TABLE 4

| Relative Quality Ratings, Mid-Florida | |
|---|---|
| 'SeaIsle Supreme' | 1.59 (best) |
| 'TE-13' | 1.75 |
| 'SeaIsle 2000' | 1.75 |
| 'SeaIsle 1' | 2.25 |

Turf density:

TABLE 5

| Relative Density Ratings, Mid-Florida | |
|---|---|
| 'SeaIsle Supreme' | 1.21 (tightest canopy) |
| 'TE-13' | 1.50 |

TABLE 5-continued

| Relative Density Ratings, Mid-Florida | |
|---|---|
| 'SeaIsle 2000' | 1.50 |
| 'SeaIsle 1' | 2.50 |
| 'SWA-4' | 9.00 (open canopy) |

Disease resistance:

TABLE 6

| Visual Dollar Spot Ratings, mid-Florida | |
|---|---|
| 'TE-13' | 1.425 (lowest) |
| 'SeaIsle 1' | 1.500 |
| 'SeaIsle 2000' | 1.750 |
| 'SeaIsle Supreme' | 3.830 (highest) |

Seed head (Inflorescence) production: 'TE-13' produces very few seed heads compared to other *paspalum* cultivars currently on the market. Table 7 shows a comparison of some of these cultivars by measuring the mean seed head exsertion.

TABLE 7

Seed Head Expression Ratings among *Paspalum* Cultivars and Experimental Ecotypes

| Cultivar | Mean |
|---|---|
| 'SeaIsle Supreme' | 1.00 (fewest) |
| 'TE-6' | 1.10 |
| 'TE-13' | 1.63 |
| 'SeaIsle 1' | 2.00 |
| 'TE-15' | 2.17 |
| 'TE-7' | 2.50 |
| 'TE-14' | 2.50 |
| 'TE-9' | 2.75 |
| 'TE-12' | 3.00 |
| 'TE-8' | 3.00 |
| 'SeaIsle 2000' | 3.17 |
| 'TE-17' | 3.25 |
| 'TE-4' | 3.50 |
| 'TE-10' | 4.00 |
| 'CHS-22' | 4.00 |
| 'CHS-23' | 4.00 |
| 'SWA-4' | 5.00 (most) |

Rating system: 1 = no seed head exsertion, 5 = excessive seed head exsertion
Minimum of 5 ratings taken at the end of Spring and the end of Summer in mid-Florida DNA analysis: DNA profile analysis that was conducted shows distinct genetic separation from 'TE-13' and other *paspalum* cultivars currently on the market. 'TE-13' is a genetically distinct and unique cultivar genetically.

DNA from 10 individual genotypes per cultivar was extracted. Three Inter Simple Sequence Repeats (ISSR) and one Random Amplification of Polymorphic DNA (RAPD) primer(s) were selected based on screening 10 primers and testing on 48 DNA samples to generate a total of nine bright and reproducible polymorphic bands. Genetic distances between all five genotypes were calculated between genotypes of each cultivar as well as among genotypes as the complement to the simple matching coefficient using the bands. These genetic distance matrices were then used to estimate two multidimensional scaling (MDS) coordinates.

Table 8 below shows results of ANOVA using first genetic coordinates estimated from genetic distances among samples of cultivars based on a multivariate analysis.

TABLE 8

| ANOVA Results of Cultivars | | | | | |
|---|---|---|---|---|---|
| Source | Nparm | DF | Sum of Squares | F Ratio | Prob > F |
| Cultivars | 4 | 4 | 5.4823519 | 28197.92 | <.0001 |
| Replication | 1 | 1 | 0.0001185 | 2.4390 | 0.1259 |

Table 9 below demonstrates that statistical differences among the 5 cultivars were detected.

TABLE 9

| Statistical Analysis | | |
|---|---|---|
| Cultivars | | Least Sq Mean |
| 'SeaIsle Supreme' | A | 0.4799059 |
| 'Salam' ™ | B | 0.2704704 |
| 'TE-6' | C | −0.1000941 |

TABLE 9-continued

| Statistical Analysis | | |
|---|---|---|
| Cultivars | | Least Sq Mean |
| 'TE-13' | C | −0.1020941 |
| 'SeaIsle2000' | D | −0.4900941 |

Levels not connected by same letter are significantly different at P = 0.05 based on LS means difference Tukey HSD.

The A through D separation indicates similarities or differences among the five cultivars. 'TE-6' and 'TE-13' exhibited a similar genetic profile, while 'SeaIsle Supreme', 'Salam'™, 'TE-13' and 'SeaIsle 2000' were genetically different from each other and therefore were determined to be genetically unique cultivars.

What is claimed:

1. A new and genetically distinct cultivar of *Paspalum vaginatum* plant named 'TE-13' as described and illustrated herein having distinguishing traits of increased growth density, good foliarly disease resistance, dark genetic color, and aggressive growth under salinity.

* * * * *